United States Patent [19]
Ober et al.

[11] Patent Number: 6,113,237
[45] Date of Patent: Sep. 5, 2000

[54] ADAPTABLE EYE MOVEMENT MEASUREMENT DEVICE

[76] Inventors: Jan Krzysztof Ober; Jan Jakub Ober, both of Ul. Brzechwy 6, Poznan, Poland, 60-195

[21] Appl. No.: 09/455,260

[22] Filed: Dec. 6, 1999

[51] Int. Cl.$^7$ ........................................................ A61B 3/14
[52] U.S. Cl. ............................................................ 351/210
[58] Field of Search .................................... 351/205, 209, 351/210, 245, 221, 158; 600/558, 595

[56] References Cited

U.S. PATENT DOCUMENTS

| | | |
|---|---|---|
| 4,102,564 | 7/1978 | Michael .................................. 351/210 |
| 4,145,122 | 3/1979 | Rinard . |
| 4,373,787 | 2/1983 | Crane . |
| 4,735,498 | 4/1988 | Udden . |
| 4,815,839 | 3/1989 | Waldorf . |
| 4,836,670 | 6/1989 | Hutchinson . |
| 4,950,069 | 8/1990 | Hutchinson . |
| 4,958,925 | 9/1990 | Ober . |
| 4,973,149 | 11/1990 | Hutchinson . |
| 4,988,183 | 1/1991 | Kasahara . |
| 5,137,345 | 8/1992 | Waldorf . |
| 5,410,376 | 4/1995 | Cornsweet . |
| 5,422,690 | 6/1995 | Rotherg . |
| 5,430,505 | 7/1995 | Katz . |
| 5,555,895 | 9/1996 | Ulmer . |
| 5,614,967 | 3/1997 | Norio . |
| 5,714,967 | 2/1998 | Okamura . |

FOREIGN PATENT DOCUMENTS

| | | |
|---|---|---|
| WO9715033A2 | 4/1997 | WIPO . |
| WO9920174A1 | 4/1999 | WIPO . |

OTHER PUBLICATIONS

Carpenter, R.H.S., Movements of the Eyes, Methods of Measuring Eye Movement, 1998, 2d Edition, Pion Ltd.
Ciuffreda, K.J., Tannen, B., Eye Movement Basics for the Clinician, Methods to Assess Eye Position and Movement, Chapt 8, 1995, Mosby.
YGGE, J., Lennerstrand, G., Eye Movements in Reading, Ober, J., Infra–red Reflection Technique, pp. 9–19, 1994, Wenner–Gren Int'l Symp Series vol. 64, Pergamon.

*Primary Examiner*—George Manuel
*Attorney, Agent, or Firm*—Francis T. Kremblas, Jr

[57] ABSTRACT

The presently disclosed invention is a device for measuring horizontal and vertical eye movement. The device is adaptable to utilize multiple measurement technologies (e.g., direct infrared, electro-oculography, ultrasound, or video), and is capable of measuring each eye individually or both eyes jointly. The present invention overcomes the shortcomings of the prior art by requiring minimal adjustment for accurate measurement, only minimally obstructing the user's visual range (i.e., slightly more than the user's own nose), being made of low cost and readily available material, and by being comprised of a comfortable and efficient design of an adjustable nose and forehead piece with an adjustable head strap. An additional advancement over the prior art is that the presently disclosed device does not require an aperture or frame, as did the prior art, or any additional optics such as, lenses, mirrors, or prisms. The device rests on the user's nose with the sensors located near the nasal area of the eye(s) utilizing a nose bridge component to house the measuring technology. The forehead piece and head strap provide for ease of alignment, added stability, and a wide range of test applications. The greater field of vision provided by this device allows for a wide range of test applications.

3 Claims, 2 Drawing Sheets

FRONT VIEW

FRONT VIEW

SIDE VIEW

ADAPTABLE EYE MOVEMENT MEASUREMENT DEVICE

BACKGROUND OF THE INVENTION

In devices used for measuring eye movement, the prior art required precise adjustments for each subject, and complete to partial blocking of the subject's visual range which detrimentally inhibited testing capabilities. Certain versions of these devices limited the subject's mobility by requiring the subject to remain perfectly still during measurement. These prior devices were designed to be worn as goggles, helmets, or spectacles which housed the measurement technology.

The main types of eye movement measurement and monitoring systems in common use are: Infrared; Video; Electro-oculography; Limbus trackers; Purkinje reflection trackers, and Scleral Coil trackers. Limbus trackers are generally cheap and easy to use, but mainly only useful for measurements in one axis at a time, that is, they are not gaze monitors. For accurately assessing point of gaze the most common method is the video tracker, where the pupil or iris is imaged using a video camera and a simple image processing module extracts point of gaze, pupil diameter, and in some advanced systems ocular torsion in real time. The disadvantage of video is that generally the sampling rate is restricted to the video frame rate, making such systems less suitable for looking at parameters such as saccadic latency. Purkinje reflection trackers may also be used as gaze monitors and have a high degree of accuracy and good temporal resolution but are very difficult to set up. Finally, Scleral coil systems, in which a small coil is placed on a contact lens and its position measured within a large frame bounded by coils, allow measurement of point of gaze and ocular torsion at high spatial and temporal resolutions. However, Scleral coils are invasive, such that a hard annular contact lens must be attached directly to the eye, which typically has a maximum wearing time of 30 minutes.

The present invention overcomes the shortcomings of the prior art by requiring minimal adjustment for accurate measurement, only minimally obstructing the user's visual range (e.g., slightly more than the user's own nose), being made of low cost and readily available material, and by being comprised of a comfortable and efficient design of an adjustable nose and forehead piece with an adjustable head strap. The presently disclosed device does not require an aperture or frame as did the prior art, or any additional optics such as, lenses, mirrors, or prisms.

BRIEF SUMMARY OF THE INVENTION:

The purpose of the disclosed invention is to provide the means for measuring horizontal and vertical movement of the eye(s). The present invention is directed to an eye movement measurement device that satisfies the adjustability, alignment, design, and measurement needs identified in the BACKGROUND section above.

This object is accomplished by disclosing an eye movement measurement device, and versions thereof, capable of measuring the horizontal and vertical movement of one eye independently, or measuring both eyes jointly. The device is adaptable to multiple measurement technologies, such as direct infrared, electro-oculography, video, and ultrasound.

The device rests on the nose and forehead of the user, and an adjustable head strap secures the device and aids in alignment FIGS. 1A and 1B. Minimal adjustment or alignment is required for accurate measurement: the angle between the nose bridge FIGS. 1A4 and 1B4 and forehead piece FIGS. 1A6 and 1B6 can be adjusted by using the hinge between the two FIGS. 1A5 and 1B5, for alignment, accurate measurement, and user comfort. The nose bridge and forehead piece are designed to minimally obstruct the user's field of view only slightly more than the user's nose would obstruct FIG. 1A. This minimal obstruction allows for a greater range of tests to be performed. Attached to the forehead piece is an adjustable head strap FIG. 1A7 and 1B7 for alignment, accurate measurement, and user comfort which secures the device to the user's head allowing for a greater range of tests to be performed. The measuring and calculating technology are suitably attached to the nose piece and forehead plate.

BRIEF DESCRIPTION OF THE SEVERAL VIEWS OF THE DRAWINGS

FIGS. 1A and 1B are for the Official Gazette.

DETAILED DESCRIPTION OF THE INVENTION

The invention disclosed herein relates to a device for measuring eye movement which is adaptable for and capable of utilizing multiple sensing means.

The prior art required precise adjustments for each subject, and complete to partial blocking of the subject's visual range which detrimentally inhibited testing capabilities. Certain devices limited the subject's mobility by requiring the subject to remain perfectly still during measurement. These prior devices were designed to be worn as goggles, helmets, or spectacles, which housed the measurement technology.

The present invention overcomes the shortcomings of the prior art by requiring minimal adjustment for accurate measurement, only minimally obstructing the user's visual range (i.e., slightly more than the user's own nose), being made of low cost and readily available material, and by being comprised of a comfortable and efficient design of an adjustable nose and forehead piece with an adjustable head strap. An additional advancement over the prior art is that the presently disclosed device does not require an aperture or frame, as did the prior art, or any additional optics such as, lenses, mirrors, or prisms.

Figure 1A:
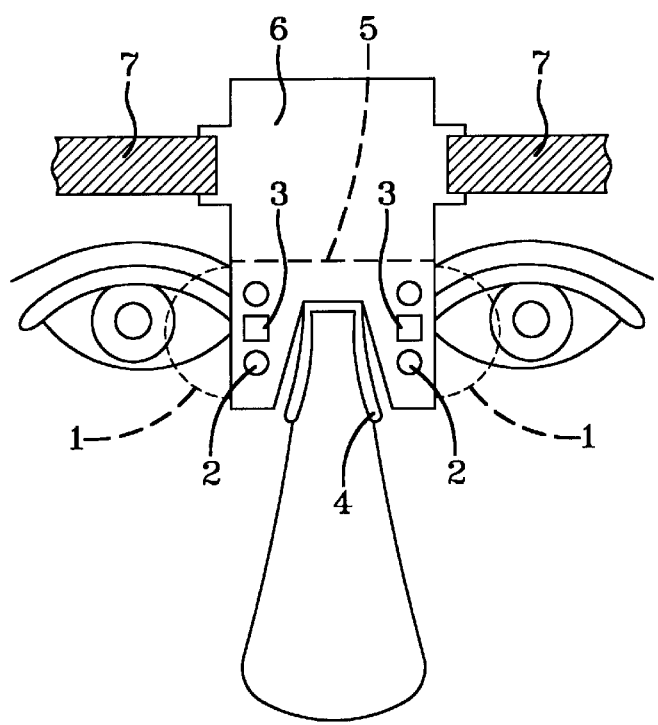
FIG. 1A shows a front view of the first preferred embodiment of the device and its components. Component "1" shows the area of the eye measured. Component "2" shows the illuminators. Component "3" shows the sensors. Component "4" shows the nose bridge piece. Component "5" shows the adjustable portion of the mounting structure. Component "6" shows the forehead piece. Component "7" shows the adjustable head strap.
Figure 1B:
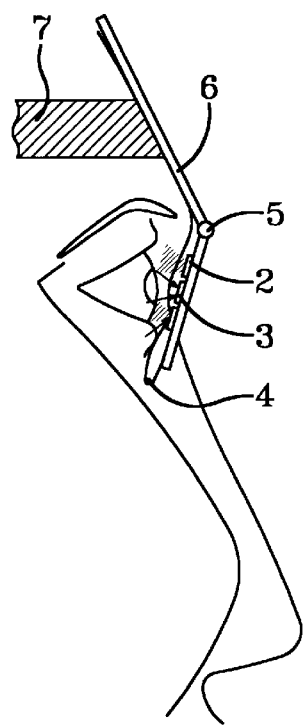
FIG. 1B shows a side view of the first preferred embodiment of the device and its components "2", "3", "4", "5", "6" and "7" from FIG. 1A above.
Figure 2:
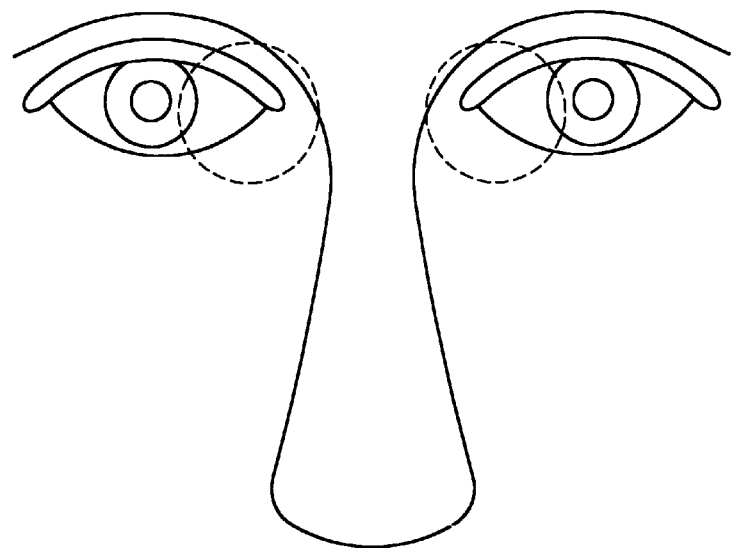
FIG. 2 shows a front view of the area of the eye measured by the first preferred embodiment. The area is outlined by dashed circles.

A. Preferred Embodiments:

The preferred embodiment of the presently disclosed eye movement measuring device is comprised of an adjustable mounting structure, sensing means, and measurement calculation means FIGS. 1A and 1B. The device is adaptable to and capable of utilizing multiple kinds of sensing technology.

The adjustable mounting structure is comprised of a nose bridge component FIG. 1A4, a forehead plate FIG. 1A6, adjustment means FIG. 1A5, and an adjustable head strap FIG. 1A7. The nose bridge component FIG. 1A4, which is similar to the bridge support on common eye glasses, rests on the user's nose. The proprietary design of the nose bridge and forehead plate FIG. 1A6 minimally obstructs the user's field of vision, whereby, the only portion of the user's visual range which is obstructed is slightly more than what the user's own nose would obstruct FIG. 1A. Thus, a wider variety of tests can be performed on the user than with the prior art devices. The forehead plate FIG. 1A6 extends above the nose bridge support component FIG. 1A4 and is attached to the nose bridge FIG. 1A4 by suitable adjustable means FIG. 1A5. The adjustable means may consist of hinges, screws, or springs for adjustability between the nose bridge component and the forehead plate component. The adjustable head strap FIG. 1A7 is attached to the forehead plate FIG. 1A6. The adjustable head strap FIG. 1A7 secures the mounting structure FIGS. 1A4 and 1A6 in place, and stabilizes and aligns the structure FIGS. 1A4 and 1A6. Head strap adjustability can be achieved using buckles, elastic material, fasteners, rings, velcro, temple arms, or other such means.

The nose bridge FIG. 1A4, forehead plate FIG. 1A6, and strap FIG. 1A7 are capable of being made with low cost and readily available materials. Therefore, the presently disclosed device has the advantage of increased accessibility by practitioners, professionals, and researchers alike, thus has increased usefulness over the prior art.

The presently disclosed device is capable of measuring horizontal and vertical eye movement utilizing multiple sensing technologies. For example, this device is capable of being outfitted with direct infrared, electro-oculography, ultrasound, or video technology, as well as being adaptable to various other technologies.

Figure 3A:
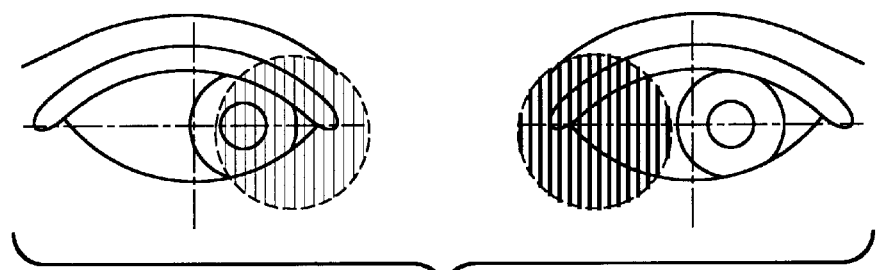
FIG. 3 shows a front view of the measured areas of the first preferred embodiment as the eyes move from side to side. The lighter shading represents more light being reflected when the eye's corneal bulge moves closer to the sensors.
Figure 3B:
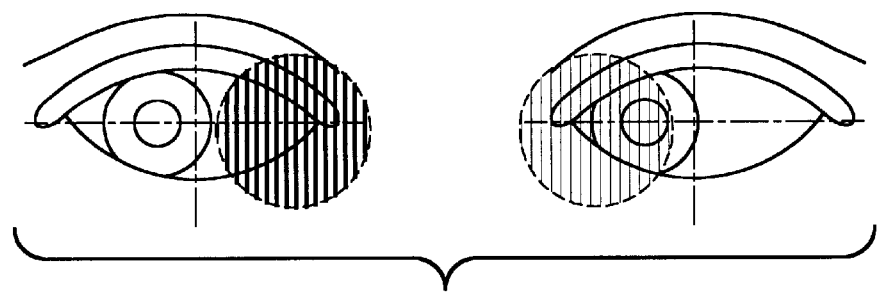

The first preferred embodiment utilizes direct infrared illumination and sensing means FIGS. 1A, 1B, 2, 3. In this version, the nasal portion of one or both eyes is illuminated FIGS. 1A, 1B, 2, 3, and sensors FIG. 1A3 are used to measure the amount of reflected light. For example FIG. 3, as the corneal bulge (i.e., the protruding spherical cornea) moves away from the light source(s) FIG. 1A2 (or illuminator(s)), less light is reflected to the light detector(s) FIG. 1A3 (or photodiode(s), or sensor(s)). The illuminator(s) FIG. 1A2 and sensor(s) FIG. 1A3 are attached to the nose bridge component FIG. 1A4 of the adjustable mounting structure FIGS. 1A4 and 1A5. The measurement principle is based on taking the differences between the averages of reflected light from the nasal areas of the eyes FIGS. 1A1, 2, 3.

Infrared measurement is preferred over electro-oculography because infrared produces higher resolution and is capable of measuring smaller eye movements. Congruently, infrared has less noise and base line drift than electro-oculography.

Infrared measurement is preferred over video means based on a cost versus performance analysis. The production and sales cost for infrared measurement technology is significantly lower than the costs for video technology, whereas the performance capabilities and measurement quality of either infrared or video are similar.

Another preferred embodiment would utilize electro-oculography. In one version, on each side of the subject's nose, a titanium sensor element would be attached to the nose bridge so that it contacts the subject's skin. Titanium is the preferred material because of its noncorrosive and nonallergic properties. The sensor would measure eye movement through the skin via change of the distribution of electro-oculographic potential. Attached to the forehead piece would be a third contact, serving the reference electrode and grounding purposes.

Other versions of preferred embodiments would utilize ultrasound, video, or other technologies.

The various measuring technologies are compact and miniaturized enough, and the proprietary design of the device simplified, so that even when adapted with different technologies, none would interfere with the minimal alignment, minimal field of view obstruction, and comfortable, light weight advantages of the nose bridge FIG. 4 and forehead plate FIG. 6 mounting means.

The measuring and calculating means are attached to the nose and forehead structure mounting means FIGS. 1A4 and 1A6. The technology used requires minimal power to average the horizontal measurements, or average the vertical measurements, or compute a combined horizontal and vertical average (omnidirectional measurement), or measure and compute the left and right eye separately. Therefore, the device is capable of running off a small battery and capable of completely standing alone by utilizing wireless transmission means. Alternatively, versions of the device would utilize an external power supply, as well as a data transmission cable.

Thus, the above disclosed eye movement measurement device has advantages, capabilities, qualities, and usefulness not contemplated by the prior art.

B. Applications:

The presently disclosed device is capable of measuring horizontal and vertical eye movement using multiple kinds of technologies with only minimal restriction of the user's testable field of view and movement FIGS. 1A and 1B. The low cost design further allows greater usefulness via easier access to the device by practitioners, professionals, and researchers.

Therefore, the device's uses range from communications to entertainment, and from medical to military applications. The adaptability of different technologies allows for an even greater range of applications for the device. Thus, depending on the accuracy and type of measurement required, different technologies can easily be interchanged on the device, such as, infrared illuminators and sensors FIGS. 1A, 1B, 2, 3, electronic sensors, video monitors, ultrasound, or other technologies.

The proprietary simplicity of the design allows the device to be applied in controlled environments, as well as field environments. The following list of applications is not intended to be exclusive, it is only a broad overview of uses. The broad capabilities of the device include testing for balance, neurological disorders, drug side effects, testing for drug use (e.g., alcohol), or determining the subject's state of consciousness or point of gaze for targeting or control and communications interaction of a pilot or driver. The device is equally usable on adults, children, or infants with minimal modifications and no effects on its measuring capabilities. Other benefits from this device are due to its low cost and wide applicability. Practitioners, professionals, and researchers will be able to perform a greater set of tests because of the greater quantities attainable, the light weight and comfort, and the greater field of vision offered by this device. Subjects ranging from infants to the elderly can be tested using rapid head movement or head shaking tests, in lab environments such as nuclear magnetic resonance testing, or it can be worn while performing normal daily functions.

Thus, based on the device's adaptable proprietary design which allows for a wide field of vision, minimal adjustment and alignment needs, stability and accuracy due to the head strap, and the device's light weight comfort, it is only limited by the available measuring technology and the foreseeable uses.

We claim:

1. A device for measuring the movement of both eyes independently and simultaneously utilizing sensors placed approximately at the nasal location;
   a. Said device averages the horizontal measurements, or averages the vertical measurements, or calculates a combined horizontal and vertical average, or measures and calculates the left and right eye separately.

2. The device of claim 1, where the sensors are located approximately adjacent to the nose so that the field of view is minimally obstructed, except by the nose itself, comprised of;
   a. Adjustable mounting means consisting of nasal and forehead components;
   b. Said mounting means placed on the flat surface of the forehead along with a nasal bridge support which aligns the sensor(s) on the symmetry axis of the nose;
   c. An adjustable head strap attached to the mounting means that goes around the top portion of the head and exerts a pulling force to stabilize the forehead mounting means and aligns the mounting structure along the horizontal axis.

3. A device as in claim 1, which is capable of measuring by utilizing electro-oculography means, video means, infrared means, or ultrasound means, consisting of;
   a. Adjustable mounting means consisting of nasal and forehead components;
   b. Said mounting means placed on the flat surface of the forehead along with a nasal bridge support which aligns the sensor(s) on the symmetry axis of the nose;
   c. Said mounting means contoured to the face so the sensors are located approximately adjacent to the nose so that the field of view is minimally obstructed, except by the nose itself; and
   d. An adjustable head strap attached to the mounting means that goes around the top portion of the head and exerts a pulling force to stabilize the forehead mounting means and aligns the mounting structure along the horizontal axis.

* * * * *